US012673092B2

(12) United States Patent
Tepic et al.

(10) Patent No.: US 12,673,092 B2
(45) Date of Patent: Jul. 7, 2026

(54) ASPARAGINASE-BASED CANCER THERAPY

(71) Applicant: Kyon Biotech AG, Zürich (CH)

(72) Inventors: Slobodan Tepic, Zürich (CH); Goran Cvetkovic, Rapperswil-Jona (CH)

(73) Assignee: KYON BIOTECH AG, Zürich (CH)

( * ) Notice: Subject to any disclaimer, the term of this patent is extended or adjusted under 35 U.S.C. 154(b) by 654 days.

(21) Appl. No.: 17/616,547

(22) PCT Filed: May 29, 2020

(86) PCT No.: PCT/EP2020/064957
§ 371 (c)(1),
(2) Date: Dec. 3, 2021

(87) PCT Pub. No.: WO2020/245041
PCT Pub. Date: Dec. 10, 2020

(65) Prior Publication Data
US 2022/0249629 A1 Aug. 11, 2022

(30) Foreign Application Priority Data
Jun. 4, 2019 (EP) ..................................... 19178062

(51) Int. Cl.
*A61K 38/50* (2006.01)
*A61K 31/17* (2006.01)
*A61P 35/02* (2006.01)

(52) U.S. Cl.
CPC .............. *A61K 38/50* (2013.01); *A61K 31/17* (2013.01); *A61P 35/02* (2018.01)

(58) Field of Classification Search
CPC .......... A61K 38/50; A61K 31/17; A61P 35/02
See application file for complete search history.

(56) References Cited

U.S. PATENT DOCUMENTS 3,660,238 A 5/1972 Wade

FOREIGN PATENT DOCUMENTS

WO 2008148932 A2 12/2008
WO 2018085493 A1 5/2018

OTHER PUBLICATIONS

Silverman et al., Improved outcome for children with acute lymphoblastic leukemia: results of Dana-Farber Consortium Protocol 9101. Blood. Mar. 1, 2001;97(5):1211-8. doi: 10.1182/blood. v97.5.1211. PMID: 11222362. (Year: 2001).*
Upadhyay AK, Singh A, Mukherjee KJ, Panda AK. Refolding and purification of recombinant L-asparaginase from inclusion bodies of *E. coli* into active tetrameric protein. Front Microbiol. Sep. 15, 2014;5:486. doi: 10.3389/fmicb.2014.00486. PMID: 25309524; PMCID: PMC4164012. (Year: 2014).*
Shifrin S, Parrott CL. In vitro assembly of L-asparaginase subunits. J Biol Chem. Jul. 10, 1974;249(13):4175-80. PMID: 4604589. (Year: 1974).*
Pieters R, et al., Pharmacokinetics, pharmacodynamics, efficacy, and safety of a new recombinant asparaginase preparation. Blood. Dec. 15, 2008;112(13):4832-8. doi: 10.1182/blood-2008-04-149443. Epub Sep. 19, 2008. PMID: 18805963. (Year: 2008).*
Avramis VI, Tiwari PN. Asparaginase (native ASNase or pegylated ASNase) in the treatment of acute lymphoblastic leukemia. Int J Nanomedicine. 2006;1(3):241-54. PMID: 17717965; PMCID: PMC2426805. (Year: 2006).*
Hellman K et al., "The effect of freeze-drying on the quaternary structure of l-asparaginase from Erwinia carotovora", Biochimica Et Biophysica Acta. Protein Structure and Molecular Enzymology, vol. 749, No. 2, Dec. 12, 1983, pp. 133-142.
Metayer et al., "Mechanisms of cell death induced by arginase and asparaginase in precursor B-cell lymphoblasts", Apoptosis, vol. 24, No. 1, Dec. 21, 2018, pp. 145-156.
International Search Report and Written Opinion issued in PCT/EP2020/064957 dated Aug. 27, 2020, 15 pages.
Van der Meer et al., 'In Vivo Imaging of Antileukemic Drug Asparaginase Reveals a Rapid Macrophage-Mediated Clearance from the Bone Marrow', Journ of Nuclear Medicine 58, No. 2, pp. 214-220 (2017).
Shifrin et al., 'In vitro Assembly of L-Asparaginase Subunits', J of Biol Chem 249, No. 13, pp. 4175-4180 (1974).
Metayer Lucy e et al., 'Mechanisms of Cell Death Induced by Arginase and Asparaginase in precursor B-Cell Lymphoblasts' Apoptosis 24, pp. 145-156 (2019).
Camargos Rocha et al., 'Current Strategies for the Detection of Minimal Residual Disease in Childhood Acute Lymphoblastic Leukemia', Mediterr J Hematol Infect Dis.; 8; 12 pages (2016).
Kim K. et al., 'L-Asparaginase Delivered by Salmonella Typhimurium Suppresses Solid Tumors', Molecular Therapy—Oncolytics 2, (2015), 8 pages.
Wells J. et al., 'Arginase Treatment Prevents the Recovery of Canine Lymphoma and Osteosarcoma Cells Resistant to the Toxic Effects of Prolonged Arginine Deprivation', PLOS One 8, Issue 1 (2013), 9 pages.
Paula Kiberstis, 'It takes a village', Science 363, Special Report, pp. 1164-1165 (2019).
Couzin-Frankel, 'Beyond Survival', Science 363, Special Report, pp. 1166-1169 (2019).

(Continued)

*Primary Examiner* — Louise W Humphrey
*Assistant Examiner* — Rachel Emily Martin
(74) *Attorney, Agent, or Firm* — Rothwell, Figg, Ernst & Manbeck, P.C.

(57) ABSTRACT

The present invention relates to an improved preparation and delivery of asparaginase for use in medicine, e.g. in human and veterinary medicine.

7 Claims, No Drawings

(56) References Cited

OTHER PUBLICATIONS

Sweet-Cordero et al., 'The Genomic Landscape of Pediatric Cancers Implication for Diagnosis and Treatment', Science 363, Special Report, pp. 1170-1175 (2019).

Dubois et al., 'Ushering in the Next Generation of Precision Trials for Pediatric Cancer', Science 363, Special Report, pp. 1175-1181 (2019).

Lam et al., 'Science and Health for all Children with Cancer', Science 363, Special Report, pp. 1182-1186 (2019).

Cheson et al., 'Report of an International Workshop to Standardize Response Criteria for non-Hodgkin's Lymphomas', J of Clin Oncol vol. 17, No. 4, pp. 1244-1253 (1999).

Notification of Second Office Action issued for the Chinese Patent Application No. 202080038803.X, mailed on Oct. 26, 2024, 11 pages (English translation only).

* cited by examiner

ASPARAGINASE-BASED CANCER THERAPY

CROSS REFERENCE TO RELATED APPLICATION

This application is a 35 U.S.C. 371 National Phase Entry Application from PCT/EP2020/064957, filed May 29, 2020, which claims the benefit of European Patent Application Ser. No. 19/178,062.6 filed on Jun. 4, 2019, the disclosure of which is herein incorporated by reference in its entirety.

The present invention relates to an improved preparation and delivery of asparaginase for use in medicine, e.g. in human and veterinary medicine.

BACKGROUND

Currently, there are three commercially available formulations of L-asparaginase (in the following asparaginase) in clinical use, both in human and veterinary oncology: (1) a tetramer derived from *Escherichia coli* with a molecular weight of about 140 kDa; (2) a tetramer derived from *Dickeya dadantii* (*Erwinia chrysanthemi*) of about the same molecular weight; (3) a pegylated version of (1) with about 400 kDa added to the tetramer as poly-ethylene-glycol (PEG). There is also a recombinant asparaginase produced in genetically engineered *E. coli*.

The molecular weights of all of these molecules exceed the upper limit of about 70 kDa for molecules that can be eliminated by globular filtration in kidneys. The main mechanism of asparaginase clearance from the vascular circulation is via non-specific immune response (Van der Meer, L. T., et al., *In Vivo Imaging of Antileukemic Drug Asparaginase Reveals a Rapid Macrophage-Mediated Clearance from the Bone Marrow*, The Journal of Nuclear Medicine, Vol. 58, No. 2, February 2017) in the initial weeks of therapy, followed by a specific immune response (antibody-mediated) with the onset at about 4 weeks after the start of the therapy. The in-vivo half-life of un-pegylated asparaginase reported in the literature is from about 8 to about 40 hours, depending on the mode of delivery (i.v. or i.m.) and probably on the immune status of the patient. The half-life of the pegylated form is significantly longer, in the range of 2.5 to 12 days.

The conventional preparation of asparaginase for i.v. infusion or an i.m. injection is carried out by dissolution of the lyophilized enzyme in water and, in most cases, by further dilution in physiological saline.

Due to their large molecular weight as tetramers, the asparaginase molecules are confined to the vascular circulation if delivered by intravenous (i.v.) infusion. If delivered by intramuscular (i.m.) injection asparaginase is transported via lymphatic flow into the vascular system as well, albeit with a slower rate and thus with an apparently longer elimination time. In neither delivery mode does the medication enter interstitial fluid space but in traces, which greatly limits its anti-cancer effectiveness. Modification by pegylation prolongs the half-life of the drug but makes its exit from the vascular system even less probable.

Cancerous cells (e.g. leukemia or lymphoma cells) are present within the vascular system only transiently and as a very small fraction of the total population. Thus, effectiveness of asparaginase confined to the vascular circulation in depleting asparagine in the interstitial fluid is limited due to constant inflow of asparagine into interstitial space from protein turnover and asparagine synthesis by practically all cells in the body. Diffusion of asparagine into the vascular system is limited and the molecular transport by convection between the lymphatic and vascular circulations is very modest. Consequently, a deep depletion of asparagine in the medium surrounding cancerous cells and/or within cancerous cells residing outside the vascular system is not achievable with the present modes of administering asparaginase in tetrameric form.

Monomers of asparaginase have a molecular weight of about 35 kDa and are not enzymatically active. However, we have discovered that administration of asparaginase monomers under suitable conditions, e.g. with concurrent infusion of insulin accompanied by an appropriate rate of infusion of glucose (a so-called insulin-glucose clamp) can mediate transport of the monomers out from the vascular system into the interstitial fluid and probably into most of the cells surrounding or present in that volume. After having entered the interstitial fluid, the monomers may associate and form an enzymatically active tetramer. The transport mechanisms facilitated and/or stimulated by insulin are not fully elucidated at this time, but they likely involve endocytosis by which insulin molecules themselves are transported into responding cells.

SUMMARY OF THE INVENTION

The present invention resolves the conundrum of effective delivery of asparaginase to its target by transient, reversible disassociation of the tetramer prior to infusion, augmented by the insulin-glucose clamp, which facilitates extravasation of asparaginase monomers thus preventing their removal through kidneys. Re-association into tetramers within the interstitial fluid brings the drug into the immediate vicinity of the target cancerous cells, greatly increasing its effectiveness.

Thus, a first aspect of the present invention relates to an asparaginase preparation for use in medicine, wherein a preparation comprising asparaginase in a dissociated form, particularly in form of a monomer, is administered to a subject in need thereof.

A further aspect of the present invention relates to an asparaginase preparation comprising asparaginase in dissociated form, particularly in form of a monomer, wherein said preparation is an aqueous preparation comprising urea, particularly in a concentration between about 3 mol/l to about 8 mol/l, more particularly in a concentration of about 4 mol/l to about 6 mol/l, e.g. about 5 mol/l.

Still a further aspect of the present invention relates to a method for the treatment of cancer comprising administering a therapeutically effective amount of asparaginase in a dissociated form, particularly in form of a monomer, to a subject in need thereof.

DETAILED DESCRIPTION OF PREFERRED EMBODIMENTS

The present invention is based on the observation that asparaginase may be delivered into the vascular circulation in dissociated form, particularly as a monomer. Asparaginase monomers may be produced by reversible dissociation of asparaginase tetramers in a chaotropic agent such as urea (Shifrin S and Parrot C. L., *In vitro Assembly of L-Asparaginase Subunits*, The journal of Biological Chemistry, Vol. 249, No. 13, pp. 4175-4180, 1974). If dissolved in urea of e.g. about 8 mol/l, the monomers will separate and denature. Once urea is diluted to below about 2.5 mol/l, the monomers will start to refold and re-associate into tetramers with no loss of activity.

This is the scientific basis of the invention disclosed herein. Immediate dilution of urea upon administration, e.g. by infusion (concentration in plasma is only 2.5 to 7 mmol/l) starts the process of refolding (completed within about 30 seconds) and then re-association with the characteristic time of minutes. During this time some monomers are lost via kidneys but most are removed from the vascular system by the action of insulin. The process of re-association in the interstitial fluid delivers the active form of the enzyme to the immediate surrounding of and into the cancerous cells.

This mode of preparation and delivery can greatly increase the anti-tumor effectiveness of this very important drug (Metayer, L. E., et al., *Mechanisms of cell death induced by arginase and asparaginase in precursor B-cell lymphoblasts*, Apoptosis, 2019, 24:145-156). Even as used now, it is credited with saving the lives of thousands of patients since its introduction in broad clinical use in the seventies, most notably of those with childhood acute lymphoblastic leukemia (Camargos Rocha, J. M., et al., *Current Strategies for the Detection of Minimal Residual Disease in Childhood Acute Lymphoblastic Leukemia*, a Review in Mediterranean Journal of Hematology and Infectious Diseases, 2016:8; e2016024). Asparaginase is also used to treat acute myeloid leukemia, and non-Hodgkin's lymphoma in humans and many lymphoma types in dogs.

According to the present invention, asparaginase may be combined with chemotherapies in the induction and in some cases in maintenance phases. It can, however, also be administered as a mono-therapy.

There are several publications in the recent years suggesting that asparaginase may have anti-tumor activity even in some solid tumors provided that the enzyme is delivered to the target (Kim, K., et al., *L-Asparaginase delivered by Salmonella typhimurium suppresses solid tumors*, Molecular Therapy—Oncolytics, 2015, 2, 15007; doi:10.1038/mto.2015.7). The mode of delivery disclosed herein may be of good use in these new indications for asparaginase.

Asparaginase is on the World Health Organization's List of Essential Medicines, the most effective and safe medicines needed in a health system.

According to the present invention, a preparation of asparaginase in dissociated form, particularly in form of a monomer is provided. This preparation is typically a solution, particularly an aqueous solution. In certain embodiments, the preparation comprises dissociated asparaginase, e.g. as monomers, and a chaotropic agent for maintaining the asparaginase in its dissociated state. The chaotropic agent is present in a concentration, which is sufficient for maintaining the dissociated form of asparaginase. A preferred chaotropic agent is urea, which may be present in a concentration of about 3 mol/l to about 8 mol/l, particularly in a concentration of about 4 mol/l to about 6 mol/l, e.g. about 5 mol/l. In addition to the chaotropic agent, further pharmaceutically acceptable excipients, e.g. buffers, surfactants etc. may be present.

The asparaginase preparation of the present invention may be prepared from any available asparaginase, e.g. asparaginase produced in a bacterial cell such as *Escherichia coli* or *Dickeya dadantii*, including a recombinant asparaginase, by dissolving said asparaginase in a chaotropic agent under conditions to provide asparaginase in a dissociated form, particularly in form of monomers. The concentration of asparaginase in the preparation may be adjusted according to the particular application. For example, the concentration of asparaginase may be between about 1,000 IU/ml and about 100,000 IU/ml, e.g. about 2,000 IU/ml to about 10,000 IU/ml. The dose to be administered to a human subject in need thereof will typically be in the range of about 500 to about 5,000 IU asparaginase per kg body weight per day, depending on the subject and the disorder to be treated. Typically, the dose to be administered to a human patient will be about 2,500 IU/kg/day. For dogs, the dose is approximately doubled, i.e. about 1,000 to about 10,000 IU asparaginase per kg body weight per day, typically about 5,000 IU/kg/day.

The preparation may be administered by intravenous infusion, e.g. for a time period between about 4 and about 144 hours depending on the subject and the disorder to be treated. Other modes of administration can also be used.

In particular embodiments, the asparaginase is administered under conditions wherein transport of proteins, particularly of asparaginase monomers, from the vascular system into interstitial fluid is promoted. This can be achieved, for example, in cases, wherein the subject to whom the asparaginase preparation is administered is provided with insulin and sufficient levels of glucose to promote insulin activity. The insulin may be any type of insulin, e.g. human insulin, an animal insulin, or an insulin analogue, including insulin analogues with short half-life and with long half-life. Glucose may be provided to the subject to maintain a normal level of plasma glucose concentration, e.g. by infusion. In particular embodiments, the asparaginase preparation is co-administered with an insulin-glucose clamp, i.e. co-administration of insulin and glucose. Administration of glucose may be accompanied by administration of a potassium salt such as KCl to compensate for potassium ions entering cells if a high dose of glucose is administered.

The treatment may be supported by concomitant administration of essential amino acids, electrolytes, fluids and/or antibiotics.

The preparation of the present invention is suitable in the treatment of cancer, e.g. in human medicine or in veterinary medicine, for example in the treatment of cats and dogs. The preparation may be administered e.g. to human patients suffering from a leukemia or a lymphoma, e.g. acute lymphoblastic leukemia, acute myeloid leukemia or Non-Hodgkin's lymphoma, or to animal patients suffering from a leukemia or a lymphoma. The preparation, however, may also be used for the treatment of solid tumors such as colon cancer, breast cancer, and pancreatic cancer (Kim, K., et al., *L-Asparaginase delivered by Salmonella typhimurium suppresses solid tumors*, Molecular Therapy—Oncolytics, 2015, 2, 15007; doi:10.1038/mto.2015.7).

Further, the present invention shall be explained in more detail by the following examples:

Example 1—A Case Report

A 12 kg, 3-year-old French bulldog, diagnosed with a high grade, stage 3 lymphoma confirmed by a lymph node biopsy was treated with *E. coli* asparaginase prepared and delivered according to this invention.

90,000 IU of asparaginase were prepared in batches of 10,000 IU by dissolution in 6 ml of 8 mol/l urea, further diluted to 4 mol/l and delivered by continuous infusion over 48 hours together with short half-life insulin (at 6 IU/kg/day) and glucose as needed to maintain normal level of plasma glucose concentration (50% glucose, at 12 to 33 ml/h).

An antibiotic was delivered by an s.c. injection once a day. An antiemetic drug was also given once a day by adding it into the infusion line. No food was offered during those two days. Ringer solution was administered by infusion to maintain fluid balance. Replacement infusions of potassium chloride and/or potassium phosphate were given as needed by adding respective salts to Ringer solution.

All infusions were delivered via a central venous catheter using two syringe pumps (for insulin and asparaginase) and two peristaltic pumps (for glucose and Ringer solution). Asparaginase was delivered via its own infusion line to prevent dilution of urea prior to entry into the catheter. Samples of blood and urine were taken twice daily.

Vital signs, hematology and biochemistry showed no abnormalities during the treatment and there was no evidence of hypersensitivity. At day two there was a clear reduction of enlarged lymph nodes. Two days after the treatment a lymph node was resected—histopathology was negative. No other drugs were administered before or after asparaginase. Four weeks after the treatment the dog had no clinical signs of lymphoma.

The activity of asparaginase was measured in serum samples. In comparison to another dog treated with 6 times lower dose of asparaginase per kg body weight but without dissolution in urea, activity in serum was now two times lower. This is a strong indication that asparaginase delivered dissolved in urea was removed from vascular circulation, as intended. Some activity was also measured in urine, as expected (asparaginase monomers filtered by kidneys could re-associate in urine) but contrary to findings with conventional use of asparaginase. Plasma concentration of asparagine was lowered to below detection by conventional amino acid analysis.

About 70% of lymphoma cases in dogs are known to respond to asparaginase. Our own in vitro work comparing arginase to asparaginase (Wells, J., et al., *Arginase Treatment Prevents the Recovery of Canine Lymphoma and Osteosarcoma Cells Resistant to the Toxic Effects of Prolonged Arginine Deprivation*, PLOS One, January 2013, Vol. 8, Issue 1, e54464) is broadly in agreement with this clinical experience.

Thus, there is a great urgency to treat human and veterinary patients, especially if this modification of asparaginase can lead to a successful mono-therapy and thus reduce the incidence of long-term side effects now known to be caused by conventional chemotherapy treatments of childhood leukemia (Science, special report, Mar. 15, 2019).

Example 2—Clinical Trial Protocol

Based on the promising results shown in Example 1, a clinical trial protocol was developed.

The goal of this clinical trial is to examine whether a denatured asparaginase and its delivery to cancerous dogs (i.e. canine lymphoma patients) can lead to a longer survival than the established, standard therapy. A native molecule of asparaginase is a tetramer with a molecular weight of 140 kDa. A molecule of this size is not able to leave circulation and come close to cancer cells to attack them. Administration of reversibly dissociated asparaginase monomers in a patient, which is concurrently treated with insulin-glucose clamp, will lead to extravasation of asparaginase molecules, which will then at least partially re-associate in the extracellular space and attack cancer cells directly.

Study Design

I) Preliminary Examination

The dog will be examined (physical examination, blood CBC and biochemistry), fine-needle aspiration (FNA) and/or biopsy.

6

II) Eligibility Criteria

Only dogs that fulfill the following criteria are eligible for the treatment:

1. Diagnosis with lymphoma for which any current treatment (surgery, chemotherapy, radiation therapy, (neo) adjuvant chemotherapy or other therapies) has a low probability of achieving tumor control, functional results and cosmetic outcome.

2. No previous treatment with any form of conventional or experimental drug, which may have compromised normal organ and bone marrow function.

3. Age ≥1 year, <10 years.

4. Life expectancy of greater than six months at start of study (if they were healthy).

5. Normal laboratory and physical parameters as defined below:

Platelets: ≥150,000/μl
Glucose: ≤6 mmol/l
Creatinine: ≤100 μmol/l
Liver enzymes AST (SGOT)/ALT (SGPT): ≤5× institutional upper limit of normal.
Temperature: 38.3-39.2° C.
Pulse rate: small breed 90-160; middle breed 80-130
Exhalation 10-30/minute in rest III) Exclusion Criteria 1. Chemotherapy or radiotherapy within 4 weeks (6 weeks for nitroso-ureas or mitomycin C) prior to entering the study or lack of recovery from adverse events due to agents administered more than 4 weeks earlier.

2. Previous treatment with any other investigational agents or steroid therapy within two weeks of sampling.

3. History of allergic reactions attributed to compounds of similar chemical or biologic composition to agents used in present study including enzyme allergy.

4. History of diabetes.

5. Uncontrolled intercurrent illness including, but not limited to, ongoing or active infection, symptomatic congestive heart failure, cardiac arrhythmia or anxiety.

6. Pregnancy and lactation.

7. Esophageal disorder (e.g. esophageal stricture, esophagitis, and mega esophagus) or following esophageal foreign body removal or esophageal surgery.

8. Presence of ileus, significant GI hemorrhage, hemodynamic instability, uncontrollable vomiting and a decreased level of consciousness.

IV) Treatment Protocol

1. Administration of a standard dose of asparaginase (10,000 IU) to test the sensitivity of the tumor and the potential hypersensitivity of the dog to asparaginase.

2. Placement of a Central Venous Catheter (CVC) in general anesthesia.

3. Monitoring recovery from anesthesia.

4. On the next day, start of drug infusions (asparaginase, insulin and glucose) via previously prepared infusion pumps.

5. Monitoring 24/7 for up to maximum of 96 hours.

6. Stop of infusions.

7. Return to normal life with his owner(s).

The dog will be fasted before general anesthesia and during the treatment. Parenteral food (glucose, amino acids) and fluid will be given.

The dog will be under general anesthesia during insertion of the CVC and, if necessary, treated with pain medication (NSAID).

Each dog will be under treatment for 96 h: 12 h for the preparation, 72 h for the therapy itself and 12 h for tapering off the protocol and the follow up.

There will be 10 dogs in total.

The dogs will be constantly monitored. Any indication of pain, discomfort and symptoms is monitored, documented and treated.

Dog Preparation

I) Lymphoma Diagnosis

A diagnostic evaluation will be performed according to Withrow & MacEwen, (Canine Lymphoma and Lymphoid Leukemias, Third Edition) including signalment, history and physical examination. Further, a complete blood count (CBC) with a differential cell count, platelet count and a serum biochemistry profile will be obtained. An entire lymph node, e.g. the prescapular or popliteal lymph node, will be removed and histopathologically evaluated by an independent pathologist. Furthermore, thoracic and abdominal radiographs and ultrasonography including ultrasound, guided fine-needle aspirate cytology and/or needle biopsy will be performed.

II) Lymphoma Staging

After diagnosis, the extent of disease will be determined and correlated with the clinical stage of disease. Most dogs are presented in advanced stages (III-IV) according to the WHO's Clinical Staging System for Lymphosarcoma in Domestic Animals.

III) Catheters

A central venous catheter (CVC) and standard cephalic vein catheter (e.g. Surflo i/v. catheter, 20 G, 1¼", Terumo) will be inserted.

IV) Clistir

A whole bowel irrigation (WBI) will be performed 24 hours before the treatment starts. One day before the WBI, the dog is given antibiotics (a combination of vancomycin and gentamycin) for gut sterilization.

Medicaments

I) L-Asparaginase

L-asparaginase (Kyowa Kirin) will be administered in a dose of 4,000 IU/kg/day (or 2 ml/kg/day with 10,000 IU dissolved in 5 ml 5 mol/l urea), via CVC and an Injectomat Agilia® syringe pump.

II) Insulin 2 ml (200 IU) Insulin (Novo Nordisk)) will be diluted with 48 ml saline (200 IU/50 ml=4 IU/ml) and administered in a dose of 6 to 12 IU/kg/day, via an Injectomat Agilia®.

III) Glucose

Insulin will immediately decrease the blood glucose level unless a sugar source is provided. A 50% glucose preparation enriched with KCl is administered in a dose of 14 g/kg/day at beginning (for 25 kg dog=>30 ml/h), then according to glycemia, via an Agilia® Large Volume Pump.

IV) Essential Amino Acids

An amino acids solution for parenteral nutrition, e.g. Aminoven (Fresenius Kabi) is administered in a dose of 1 g/kg/day, i/v, via Agilia® Large Volume Pump.

V) Antibiotics

Vancomycin (Vancocin®, Eli Lilly) 5 mg/kg/day and gentamicin 2 mg/kg/day are given for gut sterilization after bowel irrigation through a feeding tube. A cephalosporin e.g. cefotaxim (Claforan®, Aventis) 25 to 50 mg/kg, every 12 hours or cefazolin natrium (Kefzol®, Eli Lilly) equal to 1 g, divided in four dosages will be administered i/v. as a prophylactic antibiotic drug for the whole treatment (for six days).

VI) Ringer Lactate

An electrolyte source e.g. Ringer lactate, will be used to balance the fluid and electrolyte needs. It will be administered in a dose of 1.5 to 3 ml/kg/h, i/v. via an infusion pump.

The dosage and total volume of Ringer lactate is calculated according to the patient's total need for water and electrolytes (60 ml/kg/d).

VII) Potassium Chloride

KCl will be added to the 50% glucose solution in a dose of 20 mmol/L.

VIII) Diuretic

A diuretic e.g. furosemide (Lasix®) will be administered in a dose of 2-6 mg/kg, 4 times a day i/v. to maintain diuresis, if needed.

IX) Propofol

Propofol (Fresenius Kabi) will be used for induction of general anesthesia and administered in a dose of 1 to 2 mg/kg, i.v. initially, and 0.4 mg/kg/h for the maintenance of the anesthesia.

Assessment of Treatment Response

The treatment response will be objectively assessed with the same procedures used for diagnosis, grading and staging of the cancer.

In human oncology, criteria for lymphoma treatment assessment are standardized as the International Workshop Criteria (IWC) for response assessment, proposed by Cheson et al. (Report of an international workshop to standardize response criteria for non-Hodgkin's lymphomas) and include five designations:

1. Complete response (CR) is the complete disappearance of all detectable evidence of disease on CT, and all disease-related symptoms, and normalization of biochemical abnormalities, and normal bone marrow biopsy (BMB). Previously involved nodes on CT more than 1.5 cm in their greatest axial diameter must regress to less than 1.5 cm, and previously measured nodes of 1.1 to 1.5 cm must decrease to less than 1 cm.

2. CRu (uncertain) corresponds to CR criteria but with a residual mass more than 1.5 cm in greatest axial diameter that has regressed by more than 75%.

3. Partial response (PR) is at least 50% reduction in the sum of the product of the greatest diameters (SPD) of the six largest nodes with no increase in the size of other nodes and no new sites of disease. Splenic and hepatic nodules must regress by at least 50% in the SPD. BMB is irrelevant for determination of PR.

4. Stable disease (SD) is less than a PR but is not progressive disease.

5. Progressive disease (PD) is more than 50% increase in the sum of the product of the greatest diameters of any previously abnormal node, or appearance of any new lesions during or at the end of therapy.

6. Relapsed disease (RD) is the appearance of any new lesion or increase in size of more than 50% of previously involved sites or nodes in patients who achieved CR or CRu.

Methods of Measurement

CT and MRI will be routinely used to measure target lesions selected for response assessment. Cytology and histology can be used to differentiate between PR and CR. All measurable lesions up to a maximum of five lesions per organ and ten lesions total, representative of all involved organs will be identified as target lesions and recorded and measured at baseline. Target lesions will be selected based on their size (lesions with the longest diameter) and their suitability for accurate repeated measurements (by imaging techniques or clinically). A sum of the longest diameter (LD) for all target lesions will be calculated and reported as the baseline sum LD. The baseline sum LD will be used as a reference to objectively characterize the tumor.

Response Criteria

I) Evaluation of Target Lesions

Complete Response (CR): Disappearance of all target lesions

Partial Response (PR): At least a 30% decrease in the sum of the LD of target lesions, taking as reference the baseline sum LD Progressive Disease (PD): At least a 20% increase in the sum of the LD of target lesions, taking as reference the smallest sum LD recorded since the treatment started or the appearance of one or more new lesions Stable Disease (SD): Neither sufficient shrinkage to qualify for PR nor sufficient increase to qualify for PD, taking as reference the smallest sum LD since the treatment started II) Evaluation of Non-Target Lesions Complete Response (CR): Disappearance of all non-target lesions and normalization of tumor marker level Incomplete Persistence of one or more non-target lesion(s) and/or Response/Stable maintenance of tumor marker level above the normal Disease (SD): limits Progressive Disease (PD): Appearance of one or more new lesions and/or unequivocal progression of existing non-target lesions Confirmation To be assigned a status of PR or CR, changes in tumor measurements will be confirmed by repeat assessments that should be performed no less than 4 weeks after the criteria for response are first met. Longer intervals as determined by the study protocol may also be appropriate. In the case of SD, follow-up measurements must have met the SD criteria at least once after study entry at a minimum interval (in general, not less than 6 to 8 weeks) that is defined in the study protocol.

Duration of Overall Response

The duration of overall response is measured from the time measurement criteria are met for CR or PR (whichever status is recorded first) until the first date that recurrence or PD is objectively documented, taking as reference for PD the smallest measurements recorded since the treatment started.

Duration of Stable Disease

SD is measured from the start of the treatment until the criteria for disease progression are met, taking as reference the smallest measurements recorded since the treatment started.

Response Review

An independent expert at the study's completion will review all responses.

Reporting of Results

All patients included in the study must be assessed for response to treatment, even if there are major protocol treatment deviations or if they are ineligible. Each patient will be assigned one of the following categories:

1) Complete response
2) Partial response
3) Stable disease
4) Progressive disease
5) Early death from malignant disease
6) Early death from toxicity
7) Early death because of other cause, or
8) Unknown (not assessable, insufficient data).

All of the patients who met the eligibility criteria should be included in the main analysis of the response rate. Patients in response categories 4 to 8 should be considered as failing to respond to treatment (disease progression). Thus, an incorrect treatment schedule or drug administration does not result in exclusion from the analysis of the response rate.

All conclusions will be based on all eligible patients. Sub-analyses may then be performed on the basis of a subset of patients, excluding those for whom major protocol deviations have been identified (e.g., early death due to other reasons, early discontinuation of treatment, major protocol violations, etc.). The 95% confidence intervals will be provided.

The invention claimed is:

1. A method for the treatment of leukemia or lymphoma comprising administering a therapeutically effective amount of monomeric asparaginase in urea to a subject in need thereof, wherein the monomeric asparaginase is administered by intravenous infusion.

2. The method of claim 1, wherein the monomeric asparaginase is administered to the subject under conditions which promote protein transport into the interstitial fluid.

3. The method of claim 1, wherein the monomeric asparaginase is administered to the subject under conditions wherein the subject is provided with concurrent infusion of insulin and glucose, wherein the glucose is infused as needed to maintain a normal level of plasma glucose concentration.

4. The method of claim 1, wherein the subject is a human patient.

5. The method of claim 1, wherein the subject is an animal patient.

6. The method of claim 1, wherein the monomeric asparaginase is administered to a human subject suffering from acute lymphoblastic leukemia, acute myeloid leukemia or non-Hodgkin's lymphoma.

7. The method of claim 5, wherein the subject is a cat or a dog.

* * * * *